(12) United States Patent
Bouchy et al.

(10) Patent No.: US 9,156,748 B2
(45) Date of Patent: Oct. 13, 2015

(54) PROCESS FOR CONVERSION OF PARAFFINIC FEEDSTOCKS OBTAINED FROM THE BIOMASS OF MIDDLE DISTILLATE BASES EMPLOYING AT LEAST ONE IZM-2 ZEOLITE-BASED CATALYST

(71) Applicant: IFP ENERGIES NOUVELLES, Rueil-Malmaison Cedex (FR)

(72) Inventors: Christophe Bouchy, Lyons (FR); Emmanuelle Guillon, Vourles (FR); Filipe Manuel Marques Mota, Lyons (FR)

(73) Assignee: IFP Energies Nouvelles, Rueil-Malmaison Cedax (FR)

( * ) Notice: Subject to any disclaimer, the term of this patent is extended or adjusted under 35 U.S.C. 154(b) by 0 days.

(21) Appl. No.: 13/723,580

(22) Filed: Dec. 21, 2012

(65) Prior Publication Data
US 2013/0165730 A1 Jun. 27, 2013

(30) Foreign Application Priority Data
Dec. 22, 2011 (FR) .................................. 11 04024

(51) Int. Cl.
| | | |
|---|---|---|
| *B01J 23/62* | (2006.01) | |
| *C07C 5/22* | (2006.01) | |
| *B01J 29/72* | (2006.01) | |
| *B01J 29/74* | (2006.01) | |
| *B01J 29/78* | (2006.01) | |
| *C10G 45/64* | (2006.01) | |
| *C10G 3/00* | (2006.01) | |

(52) U.S. Cl.
CPC ................. *C07C 5/226* (2013.01); *B01J 29/72* (2013.01); *B01J 29/74* (2013.01); *B01J 29/78* (2013.01); *C10G 3/46* (2013.01); *C10G 3/47* (2013.01); *C10G 45/64* (2013.01); *B01J 2229/20* (2013.01); *B01J 2229/42* (2013.01)

(58) Field of Classification Search
CPC ............ C10G 3/00; C10G 45/64; C10G 3/46; C10G 3/47; B01J 23/40; B01J 23/74; B01J 29/06; B01J 29/061; B01J 29/064; B01J 29/068; B01J 29/72; B01J 29/74; B01J 29/78; B01J 2229/20; B01J 2229/42; B01J 23/14; B01J 23/62; B01J 23/622; B01J 23/7049; C07C 5/00; C07C 5/02; C07C 5/13; C07C 5/22; C07C 5/373; C07C 5/222; C07C 5/226
USPC ......... 585/739, 240, 734, 737, 468, 470, 533, 585/639; 502/60, 64, 74
See application file for complete search history.

(56) References Cited

U.S. PATENT DOCUMENTS

| | | | | |
|---|---|---|---|---|
| 8,629,073 | B2 * | 1/2014 | Guillon et al. .................. | 502/60 |
| 8,754,247 | B2 * | 6/2014 | Cabiac et al. ................. | 554/167 |
| 8,936,717 | B2 * | 1/2015 | Guillon et al. ................ | 208/110 |
| 2009/0162264 | A1 * | 6/2009 | McCall et al. ................ | 422/187 |
| 2009/0300970 | A1 * | 12/2009 | Perego et al. ................... | 44/307 |
| 2011/0180455 | A1 * | 7/2011 | Bouchy et al. .................. | 208/49 |
| 2011/0190562 | A1 | 8/2011 | Guillon et al. | |
| 2011/0230691 | A1 | 9/2011 | Bonduelle et al. | |

FOREIGN PATENT DOCUMENTS

| | | |
|---|---|---|
| FR | 2 931 833 A1 | 12/2009 |
| FR | 2 931 834 A1 | 12/2009 |
| FR | 2 934 793 A1 | 2/2010 |
| FR | 2 934 794 A1 | 2/2010 |
| FR | 2 935 139 A1 | 2/2010 |
| WO | WO 2010015737 A1 * | 2/2010 |

OTHER PUBLICATIONS

Search Report of FR 1104024 (Jun. 7, 2012).

\* cited by examiner

*Primary Examiner* — In Suk Bullock
*Assistant Examiner* — Philip Louie
(74) *Attorney, Agent, or Firm* — Millen, White, Zelano & Branigan, P.C.

(57) ABSTRACT

The invention relates to a process for conversion of a paraffinic feedstock that has a number of carbon atoms of between 9 and 25, whereby said paraffinic feedstock is produced starting from renewable resources, employing a catalyst that comprises at least one hydrogenating-dehydrogenating metal that is selected from the group that is formed by the metals of group VIB and group VIII of the periodic table, taken by themselves or in a mixture, and a substrate that comprises at least one IZM-2 zeolite and at least one binder, with said process being carried out at a temperature of between 150 and 500° C., at a pressure of between 0.1 MPa and 15 MPa, at an hourly volumetric flow rate of between 0.1 and 10 $h^{-1}$, and in the presence of a total quantity of hydrogen mixed with the feedstock such that the hydrogen/feedstock ratio is between 70 and 2,000 $Nm^3/m^3$ of feedstock.

15 Claims, No Drawings

PROCESS FOR CONVERSION OF PARAFFINIC FEEDSTOCKS OBTAINED FROM THE BIOMASS OF MIDDLE DISTILLATE BASES EMPLOYING AT LEAST ONE IZM-2 ZEOLITE-BASED CATALYST

FIELD OF THE INVENTION

The search for new sources of renewable energy for the production of fuels constitutes a major issue. The demand for middle distillate bases, i.e., for a fraction that can be incorporated in the kerosene and diesel fuel pool, is rising quickly, particularly in Europe. The use of these new resources is a means for meeting this high demand, furthermore taking the environmental concerns into account.

Among different "alternative" pathways, the middle distillate bases produced from a paraffinic feedstock obtained from a feedstock that comes from renewable sources, and in particular vegetable oils or animal fats that are raw or that have undergone a preliminary treatment, as well as mixtures of such feedstocks, have particularly advantageous properties. Actually, said feedstocks that are obtained from renewable sources contain chemical structures such as triglycerides or esters or free fatty acids, with the structure and the hydrocarbon chain length of the latter being compatible with the hydrocarbons that are present in the middle distillates. Said feedstocks that are obtained from renewable sources produce, after hydrotreatment, paraffinic feedstocks, free of sulfur-containing compounds and aromatic compounds.

The patent application No. EP 1,681,337 A describes the transformation of such feedstocks by decarboxylation for forming paraffins that have one carbon atom less relative to the initial chemical structures. The advantage of this method as described in this patent consists in limiting the necessary hydrogen consumption. By contrast, the diesel fuel base yields are reduced. The catalysts that are used are metal catalysts.

The U.S. Pat. Nos. 4,992,605 and 5,705,722 describe processes for the production of bases for the diesel fuel pool that are produced from the direct transformation of vegetable oils (canola, palm, soybean, sunflower) or of lignocellulosic biomass into saturated hydrocarbons after hydrotreatment or hydrorefining of these products by themselves.

The liquid effluent that is obtained from these processes for hydrotreatment essentially consists of n-paraffins that can have cold strength properties that are inadequate for being incorporated into a diesel fuel and/or kerosene pool. In such a way as to improve the cold properties of this hydrotreated liquid effluent, a hydroisomerization stage is necessary for transforming the n-paraffins into branched paraffins that have better cold properties. This hydroisomerization stage is carried out on a bifunctional catalyst that has both a hydrogenating/dehydrogenating function and a Bronsted acid function. According to the incorporation rate and the cold properties targeted in the final fuel, it may be necessary to carry out a very intense hydroisomerization of the effluent. This hydroisomerization stage is generally accompanied by the production of cracking products that are too light to be incorporated into a diesel fuel and/or kerosene pool. The result is therefore a yield loss that it is desirable to minimize.

The patent applications EP 2 138 553 and EP 2 138 552 describe a process for treatment of a feedstock that is obtained from a renewable source that comprises a hydrotreateement, optionally a gas/liquid separation, optionally followed by an elimination of nitrogen-containing compounds, and a hydroisomerization in the presence of a catalyst that comprises at least one metal of group VIII and/or at least one metal of group VIB and at least one mono-dimensional 10 MR zeolitic molecular sieve, preferably selected from among the molecular sieves of the TON or EUO structural type or the molecular sieves ZSM-48, ZBM-30, IZM-1, COK-7, EU-2 and EU-11. Said processes make it possible to obtain high diesel fuel base yields.

The research work carried out by the applicant led him to discover that, in a surprising way, the use of an IZM-2-zeolite-based catalyst in a process for hydroconversion of a paraffinic feedstock produced from renewable resources makes it possible to obtain good middle distillate base yields and in particular to limit the production of light cracked products that cannot be incorporated into a diesel fuel and/or kerosene pool.

One objective of this invention is therefore to provide an IZM-2-based catalyst that is very selective in hydroisomerization for the conversion of a type of paraffinic feedstock that has a number of carbon atoms of between 9 and 25 and produced from renewable resources, making it possible to limit the production of light cracked products that cannot be incorporated into a diesel fuel and/or kerosene pool and therefore to improve the selectivity toward the middle distillate base production.

OBJECT OF THE INVENTION

This invention relates to a continuous process for conversion of a paraffinic feedstock that is produced from renewable resources of middle distillate bases (diesel fuel and/or kerosene).

In particular, one object of this invention is a process for conversion of a paraffinic feedstock that has a number of carbon atoms of between 9 and 25, whereby said paraffinic feedstock is produced from renewable resources, employing a catalyst that comprises at least one hydrogenating-dehydrogenating metal that is selected from the group that is formed by the metals of group VIB and group VIII of the periodic table, taken by themselves or in a mixture, and a substrate that comprises at least one IZM-2 zeolite and at least one binder, whereby said process is carried out at a temperature of between 150 and 500° C., at a pressure of between 0.1 MPa and 15 MPa, at an hourly volumetric flow rate of between 0.1 and 10 $h^{-1}$, and in the presence of a total quantity of hydrogen mixed with the feedstock such that the hydrogen/feedstock ratio is between 70 and 2,000 $Nm^3/m^3$ of feedstock.

One object of the invention is to provide a process for conversion of a paraffinic feedstock that is produced from renewable resources that make it possible to produce middle distillate bases, in particular a kerosene base and/or a diesel fuel base, while limiting the production of light products that cannot be incorporated into said bases.

Another object of the invention is to improve the degree of branching by hydroisomerization of the paraffinic feedstock that is used and produced from renewable resources, with the degree of branching being adjusted in such a way as to obtain, for the middle distillate bases, properties, in particular cold properties, that are compatible with the applicable standards for the middle distillates.

The invention also offers the advantage of providing a process that makes possible the production of middle distillate bases corresponding to the new environmental standards, starting from feedstocks obtained from renewable sources.

The diesel fuel bases that are produced are of excellent quality:
  They have a low content of sulfur, nitrogen, and aromatic compounds, An excellent cetane, because of the substantially paraffinic structure of the formed hydrocarbons, Good cold strength properties owing to the degree of isomerization of the paraffins of the fraction, A low density (generally less than 800 kg/m$^3$), which is an advantage to the extent that this facilitates the diesel fuel pool obtaining the specification of the material that is at most 845 kg/m$^3$.

The kerosene bases that are produced are of excellent quality:

They have a low content of sulfur and nitrogen,

An excellent smoke point owing to the low content of aromatic compounds,

Good cold strength properties owing to the degree of isomerization of the paraffins of the fraction, A low density (generally less than 800 kg/m$^3$).

SUMMARY OF THE INVENTION

The invention relates to a process for conversion of a paraffinic feedstock that has a number of carbon atoms of between 9 and 25, whereby said paraffinic feedstock is produced from renewable resources, excluding paraffinic feedstocks obtained by a process that involves a stage for upgrading by the Fischer-Tropsch method, whereby said process uses a catalyst that comprises at least one hydrogenating-dehydrogenating metal that is selected from the group that is formed by the metals of group VIB and group VIII of the periodic table, taken by themselves or in a mixture, and a substrate comprising at least one IZM-2 zeolite and at least one binder, whereby said process is carried out at a temperature of between 150 and 500° C., at a pressure of between 0.1 MPa and 15 MPa, at an hourly volumetric flow rate of between 0.1 and 10 h$^{-1}$, and in the presence of a total quantity of hydrogen that is mixed with the feedstock such that the hydrogen/feedstock ratio is between 70 and 2,000 Nm$^3$/m$^3$ of feedstock.

DESCRIPTION OF THE INVENTION

In accordance with the invention, said paraffinic feedstock that has a number of carbon atoms of between 9 and 25 used in the process according to the invention is produced from the renewable resources.

Preferably, said paraffinic feedstock has a number of carbon atoms of between 10 and 25, and preferably between 10 and 22.

The paraffin content in said feedstock that is used in the process according to the invention is advantageously greater than 90% by weight, preferably greater than 95% by weight, and in an even more preferred manner greater than 98% by weight.

In accordance with the invention, said feedstock that is used in the process according to the invention is a paraffinic feedstock that is produced from renewable resources, excluding paraffinic feedstocks obtained by a process that involves a stage for upgrading by the Fischer-Tropsch method. Thus, the paraffinic feedstocks that are obtained, according to a Fischer-Tropsch synthesis process, from a synthetic gas (CO+H$_2$) produced from renewable resources according to the BTL method, also called "Biomass to Liquid" according to English terminology, are excluded from the feedstocks that are used in the process according to the invention. Preferably, said paraffinic feedstock is produced from renewable resources that are selected from among vegetable oils, alga or algal oils, fish oils, and fats of vegetable or animal origin, or mixtures of such feedstocks.

Said vegetable oils can advantageously be raw or refined, totally or partly, and obtained from plants that are selected from among canola, sunflower, soybean, palm, olive, coconut, copra, castor oil, cotton, oils of peanuts, flax and sea cabbage, and all of the oils obtained from, for example, sunflowers or canola by genetic modification or hybridization, with this list not being limiting. Said animal fats are advantageously selected from among lard and fats composed of waste from the food industry or obtained from catering industries. The frying oils, the various animal oils such as fish oils, suet, and lard can also be used.

The renewable resources from which is produced the paraffinic feedstock that is used in the process according to the invention essentially contain chemical structures of the triglyceride type that one skilled in the art also knows under the name of fatty acid triesters as well as free fatty acids, whose fatty chains contain a number of carbon atoms of between 9 and 25.

The structure and the length of hydrocarbon chain of the latter is compatible with the hydrocarbons that are present in the diesel fuel and the kerosene, i.e., the middle distillate fraction. A fatty acid triester is thus composed of three fatty acid chains. These fatty acid chains in triester form or in free fatty acid form have a number of unsaturations per chain, also called a number of carbon-carbon double bonds per chain, generally encompassed between 0 and 3, but they can be higher in particular for the oils obtained from algae that generally have a number of unsaturations per chain of 5 to 6.

The molecules that are present in said renewable resources that are used in this invention therefore have a number of unsaturations, expressed by triglyceride molecule, advantageously between 0 and 18. In these feedstocks, the unsaturation rate, expressed by number of unsaturations per hydrocarbon fatty chain, is advantageously between 0 and 6.

The renewable resources generally also comprise different impurities and in particular heteroatoms such as nitrogen. The nitrogen contents in the vegetable oils are generally between approximately 1 ppm and 100 ppm by weight according to their nature. They can reach up to 1% by weight in particular feedstocks.

Said paraffinic feedstock that is used in the process according to the invention is advantageously produced from renewable resources according to processes that are known to one skilled in the art. One possible method is the catalytic transformation of said renewable resources into a deoxidized paraffinic effluent in the presence of hydrogen and, in particular, hydrotreatment.

Preferably, said paraffinic feedstock is produced by hydrotreatment of said renewable resources. These processes for hydrotreatment of renewable resources are already well known and are described in numerous patents. By way of example, said paraffinic feedstock that is used in the process according to the invention can advantageously be produced preferably by hydrotreatment and then by gas/liquid separation, starting from said renewable resources as in the patent FR 2 910 483 or in the patent FR 2 950 895.

In accordance with the invention, the process is a process for conversion of said paraffinic feedstock that is produced from renewable resources employing a catalyst that comprises at least one hydrogenating-dehydrogenating metal that is selected from the group that is formed by the metals of group VIB and group VIII of the periodic table, taken by themselves or in a mixture, and a substrate comprising at least one IZM-2 zeolite and at least one binder. Preferably, said process according to the invention is a hydroisomerization process.

The catalyst that is used in the process according to the invention is advantageously of the bifunctional type, i.e., it has a hydrogenating/dehydrogenating function and a hydroisomerizing function.

Preferably, the elements of group VIII are selected from among the noble and non-noble metals of group VIII and preferably from among iron, cobalt, nickel, ruthenium, rhodium, palladium, osmium, iridium or platinum, taken by themselves or in a mixture, and in a preferred manner from among cobalt, nickel, platinum, and palladium, taken by itself or in a mixture.

In the event that the elements of group VIII are selected from among the noble metals of group VIII, the elements of group VIII are advantageously selected from among platinum and palladium, taken by themselves or in a mixture. In this case, said elements are used in their reduced form.

In the event that the elements of group VIII are selected from among the non-noble metals of group VIII, the elements of group VIII are advantageously selected from among cobalt and nickel, taken by themselves or in a mixture. Preferably, the elements of group VIB are selected from among tungsten and molybdenum, taken by themselves or in a mixture. In the event that the hydrogenating function comprises an element of group VIII and an element of group VIB, the following metal combinations are preferred: nickel-molybdenum, cobalt-molybdenum, iron-molybdenum, iron-tungsten, nickel-tungsten, cobalt-tungsten, and in a very preferred manner: nickel-molybdenum, cobalt-molybdenum, and nickel-tungsten. It is also possible to use combinations of three metals, such as, for example, nickel-cobalt-molybdenum. When a combination of metals of group VI and group VIII is used, the catalyst is then preferably used in a sulfurized form.

In the event that said catalyst comprises at least one noble metal of group VIII, the noble metal content of said catalyst is advantageously between 0.01 and 5% by weight, in a preferred manner between 0.1 and 4% by weight, and in a very preferred manner between 0.1 and 2% by weight relative to the total mass of said catalyst.

According to a preferred mode, said catalyst can also comprise tin in addition to said noble metal(s), the tin content preferably being between 0.1 and 0.5% by weight relative to the total catalyst mass.

In the event that the catalyst comprises at least one metal of group VIB in combination with at least one non-noble metal of group VIII, the metal content of group VIB is advantageously between 5 and 40% by weight of oxide relative to the total mass of said catalyst, in a preferred manner between 10 and 35% by weight of oxide, and in a very preferred manner between 15 and 30% by weight of oxide, and the non-noble metal content of group VIII is advantageously between 0.5 and 10% by weight of oxide relative to the total mass of said catalyst, in a preferred manner between 1 and 8% by weight of oxide, and in a very preferred manner between 1.5 and 6% by weight of oxide.

In accordance with the invention, said catalyst comprises a substrate that comprises at least one IZM-2 zeolite and at least one binder.

Preferably, said catalyst comprises 2 to 80% by weight of IZM-2 zeolite, in a very preferred manner from 5 to 50% by weight, and in an also preferred manner from 5 to 30% by weight relative to the total mass of said catalyst.

The IZM-2 zeolite is a crystallized microporous solid that has a crystalline structure that is described in the patent application FR 2 918 050. The process for preparation of the IZM-2 zeolite is also described in said application.

Said IZM-2 solid has a chemical composition that is expressed on an anhydrous base, in terms of moles of oxides, defined by the following general formula: $XO_2: aY_2O_3: bM_{2/n}O$, in which X represents at least one tetravalent element, Y represents at least one trivalent element, and M is at least an alkaline metal and/or an alkaline-earth metal of valence n.

X is preferably selected from among silicon, germanium, titanium, and the mixture of at least two of these tetravalent elements, very preferably X is silicon, and Y is preferably selected from among aluminum, boron, iron, indium and gallium; very preferably Y is aluminum. M is preferably selected from among lithium, sodium, potassium, calcium, magnesium and the mixture of at least two of these metals, and very preferably M is sodium. In a preferred manner, X represents silicon; the IZM-2 crystallized solid according to the invention is then an entirely silicic solid when the element Y is absent from the composition of said IZM-2 solid. It is also advantageous to use as an element X a mixture of several elements X, in particular a mixture of silicon with another element X that is selected from among germanium and titanium, preferably germanium. Thus, when the silicon is present in a mixture with another element X, the IZM-2 crystallized solid according to the invention is then a crystallized metallosilicate that has an X-ray diffraction diagram that is identical to the one described in Table 1 when it is in its calcined form. In an even more preferred manner and in the presence of an element Y, with X being silicon and Y being aluminum, the IZM-2 crystallized solid according to the invention is then an aluminosilicate. Preferably, the IZM-2 zeolite is in aluminosilicate form.

Preferably, the molar ratio of the number of silicon atoms to the number of Si/Al aluminum atoms is less than 200, preferably less than 150, and in a very preferred manner less than 120.

The IZM-2 zeolite that enters into the composition of the substrate of the catalyst according to the invention is advantageously exchanged by at least one treatment by a solution of at least one ammonium salt in such a way as to obtain the ammonium form of the IZM-2 zeolite that once calcined leads to the acid form ($H^+$) of said IZM-2 zeolite. This exchange stage can be carried out at any stage of the preparation of the catalyst, i.e., after the preparation stage of the IZM-2 zeolite, after the stage for shaping the IZM-2 zeolite by a porous mineral binder, or else after the stage for introduction of the hydrogenating-dehydrogenating metal. Preferably, the exchange stage is carried out after the stage for shaping the IZM-2 zeolite.

Said IZM-2 zeolite that enters into the composition of the substrate of the catalyst that is used in the process according to the invention is advantageously at least partly, preferably virtually totally, in acid form, i.e., in acid form ($H^+$).

According to the invention, the substrate of the catalyst that is used in the process according to the invention contains a binder. Said binder can advantageously be amorphous or crystallized. Preferably, said binder is advantageously selected from the group that is formed by alumina, silica, silica-alumina, clays, titanium oxide, boron oxide and zirconia, taken by themselves or in a mixture. It is also possible to select the aluminates. Preferably, said binder of the substrate is the alumina. In a preferred manner, said binder of the substrate is a matrix that contains alumina in all of its forms that are known to one skilled in the art, such as, for example, the aluminas of type alpha, gamma, eta, or delta. Said aluminas differ by their specific surface area and their pore volume. Said binder of the substrate preferably comes in the form of balls, grains, or extrudates.

Preferably, said catalyst comprises 5 to 98% by weight of binder, in a very preferred manner 10 to 95% by weight, and in an also preferred manner 20 to 95% by weight relative to the total mass of said catalyst.

Preparation of the IZM-2 Substrate/Binder

Shaping of the IZM2 Substrate/Binder

The substrate of the catalyst that is used in the process according to the invention can advantageously be prepared according to all of the methods that are well known to one skilled in the art.

According to a preferred preparation method, said IZM-2 crystallized zeolite can advantageously be introduced during the solubilization or suspending of the alumina compounds that are advantageously used according to the invention. Said IZM-2 crystallized zeolite can be, without this being limiting, for example, in the form of powder, ground powder, suspension, or suspension having undergone a deagglomeration treatment. Thus, for example, said crystallized zeolite can advantageously be put into a suspension that may or may not be acidulated and at a concentration that is adjusted to the final content of IZM-2 solid targeted in the catalyst that is used according to this invention. This suspension that is commonly called a slip is then mixed with the alumina compounds.

The substrate of the catalyst that is used in the process according to the invention can advantageously be shaped by any technique that is known to one skilled in the art. The shaping can advantageously be carried out by, for example, extrusion, pelletizing, by the drop ("oil-drop") coagulation method, by turntable granulation, or by any other method that is well known to one skilled in the art.

The shaping can advantageously also be carried out in the presence of the different components of the catalyst and extrusion of the mineral paste that is obtained by pelletizing, shaping in the form of balls in a rotating holding plate or in a drum, drop coagulation, "oil-drop," "oil-up," or any other known process for agglomeration of a powder that contains alumina and optionally other ingredients that are selected from among those mentioned above.

Furthermore, the substrates that are employed in the process according to this invention may advantageously have been treated as is well known to one skilled in the art by additives for facilitating the shaping and/or improving the final mechanical properties of the substrates. By way of example of additives, it is possible to cite in particular cellulose, carboxymethyl cellulose, carboxyethyl cellulose, tall oil, xanthan gums, surfactants, flocculating agents such as polyacrylamides, carbon black, starches, stearic acid, polyacrylic alcohol, polyvinyl alcohol, biopolymers, glucose, polyethylene glycols, etc.

It is advantageously possible to add or withdraw water for adjusting the viscosity of the paste that is to be extruded. This stage can advantageously be carried out at any point in the mixing stage.

To adjust the content of solid material of the paste that is to be extruded so as to make it extrudable, it is advantageously also possible to add a compound that for the most part is solid and preferably an oxide or a hydrate. In a preferred manner, a hydrate is used, and in an even more preferred manner, an aluminum hydrate is used. The fire loss of this hydrate is advantageously greater than 15%.

The extrusion can advantageously be carried out by any conventional tool that is available commercially. The paste that is obtained from mixing is advantageously extruded through a die, for example using a piston or a single-extrusion screw or a double-extrusion screw. This extrusion stage can advantageously be carried out by any method that is known to one skilled in the art.

The extrudates of the substrate according to the invention advantageously generally have a resistance to crushing of at least 70 N/cm and in a preferred manner greater than or equal to 100 N/cm.

Heat Treatment of the IZM-2 Substrate/Binder

The substrate of the catalyst employed in the process according to this invention is then advantageously subjected to a drying stage.

Said drying stage is advantageously carried out by any known technique of one skilled in the art.

Preferably, the drying is carried out under a stream of air. Said drying can also advantageously be carried out under a stream of any oxidizing, reducing or inert gas. Preferably, the drying is advantageously carried out between 50 and 180° C., in a preferred manner between 60 and 150° C., and in a very preferred manner between 80 and 130° C.

Said substrate, optionally dried, then preferably undergoes a calcination stage.

Said calcination stage is advantageously carried out in the presence of molecular oxygen, for example by carrying out a flushing with air, at a temperature that is advantageously greater than 200° C. and less than or equal to 1100° C. Said calcination stage can advantageously be done in a flushed bed, in a swept bed, or in static atmosphere. For example, the furnace that is used can be a rotary kiln or else a vertical furnace with radial flushed layers. Preferably, said calcination stage is carried out between more than one hour at 200° C. to less than one hour at 1100° C. The calcination can optionally be carried out in the presence of water vapor and/or in the presence of an acid or basic vapor. For example, the calcination can be done under partial pressure of ammonia.

Post-calcination treatments can optionally be carried out in such a way as to improve the properties, for example textural, of the substrate.

Post-Synthesis Treatments of the IZM-2 Substrate/Binder

The IZM-2 substrate/binder of the catalyst that is employed in the process according to this invention can thus optionally be subjected to a hydrothermal treatment in a confined atmosphere. Hydrothermal treatment in a confined atmosphere means a treatment by being run into the autoclave in the presence of water at a temperature that is higher than ambient temperature.

During this hydrothermal treatment, it is advantageously possible to treat the substrate. Thus, it is advantageously possible to impregnate the substrate, prior to its being run into the autoclave, with the autoclaving being done either in the vapor phase or in the liquid phase, with this vapor or liquid phase of the autoclave able to be acidic or not. This impregnation, prior to autoclaving, can advantageously be acidic or not. This impregnation, prior to autoclaving, can optionally be carried out in the dry state or by immersion of the substrate in an acidic aqueous solution. Dry impregnation is defined as bringing the substrate into contact with a solution volume that is less than or equal to the total pore volume of the substrate. Preferably, the impregnation is done in the dry state.

The autoclave is preferably a rotary-basket autoclave such as the one that is defined in the patent application EP-A-0 387 109.

The temperature during the autoclaving can be between 100 and 250° C. for a period of time of between 30 minutes and 3 hours.

Deposition of the Hydrogenating-Dehydrogenating Function

The hydrogenating-dehydrogenating function can advantageously be introduced at any stage of the preparation, in a very preferred manner after the shaping of said IZM-2 substrate/binder. The shaping is advantageously followed by calcination; the hydrogenating-dehydrogenating function can also advantageously be introduced before or after this calcination. The preparation generally ends by calcination at a temperature of 250 to 600° C. Another of the preferred methods according to this invention advantageously consists in shaping the IZM-2 substrate/binder after a mixing of the latter, then running the thus obtained paste through a die to form extrudates. The hydrogenating-dehydrogenating function can advantageously then be introduced, only in part or totally, at the time of mixing. It can also advantageously be introduced by one or more ion exchange operations on the calcined substrate.

In a preferred way, the substrate is impregnated by an aqueous solution. The impregnation of the substrate is preferably carried out by the so-called "dry" impregnation method that is well known to one skilled in the art. The impregnation can advantageously be carried out in a single stage by a solution that contains all of the constituent elements of the final catalyst.

The hydrogenating-dehydrogenating function can advantageously be introduced by one or more operations for impregnation of the substrate that is shaped and calcined by a solution that contains at least one precursor of at least one oxide of at least one metal that is selected from the group that is formed by the metals of groups VIII and the metals of group VIB, with the precursor(s) of at least one oxide of at least one metal of group VIII preferably being introduced after those of group VIB or at the same time as the latter, if the catalyst contains at least one metal of group VIB and at least one metal of group VIII.

In the event that the catalyst advantageously contains at least one element of group VIB, for example molybdenum, it is possible, for example, to impregnate the catalyst with a solution that contains at least one element of group VIB, to dry it, and to calcine it. The impregnation of the molybdenum can advantageously be facilitated by adding phosphoric acid in the solutions of ammonium paramolybdate, which makes it possible also to introduce phosphorus in such a way as to promote catalytic activity.

The following elements—boron and/or silicon and/or phosphorus—can be introduced into the catalyst at any level of the preparation and according to any technique known to one skilled in the art.

A preferred method according to the invention consists in depositing the selected promoter element(s), for example the boron-silicon pair, on the IZM-2 substrate that is shaped with the binder that may or may not be calcined, preferably calcined. For this purpose, an aqueous solution of at least one boron salt, such as ammonium biborate or ammonium pentaborate, is prepared in an alkaline medium and in the presence of oxidized water, and a so-called dry impregnation is initiated, in which the volume of the pores of the precursor is filled by the solution that contains, for example, boron. In the event that, for example, silicon is also deposited, for example, a solution of a compound of silicon of the silicone type or the silicone oil emulsion type is used.

The promoter element(s) selected from the group that is formed by silicon, boron and phosphorus can advantageously be introduced by one or more impregnation operations with excess solution on the calcined precursor.

The boron source can advantageously be boric acid, preferably orthoboric acid $H_3BO_3$, ammonium biborate or ammonium pentaborate, boron oxide, or boric esters. Boron can be introduced, for example, in the form of a mixture of boric acid, oxidized water, and a basic organic compound that contains nitrogen, such as ammonia, primary and secondary amines, cyclic amines, compounds of the pyridine family, and quinolines, and the compounds of the pyrrole family. Boron can be introduced by, for example, a solution of boric acid in a water/alcohol mixture.

The preferred phosphorus source is orthophosphoric acid $H_3PO_4$, but its salts and esters such as the ammonium phosphates are also suitable. Phosphorus can, for example, be introduced in the form of a mixture of phosphoric acid and a basic organic compound that contains nitrogen, such as ammonia, primary and secondary amines, cyclic amines, compounds of the pyridine family, and quinolines, and compounds of the pyrrole family.

Numerous silicon sources can advantageously be employed. Thus, it is possible to use ethyl orthosilicate $Si(OEt)_4$, siloxanes, polysiloxanes, silicones, silicone emulsions, halide silicates such as ammonium fluorosilicate $(NH_4)_2SiF_6$ or sodium fluorosilicate $Na_2SiF_6$. Silicomolybdic acid and its salts, and silicotungstic acid and its salts, can also be advantageously employed. Silicon can advantageously be added by, for example, impregnation of ethyl silicate in solution in a water/alcohol mixture. The silicon can be added by, for example, impregnation of a silicon compound of the silicone or silicic acid type suspended in water.

The noble metals of group VIII of the catalyst of this invention can advantageously be present totally or partially in metal and/or oxide form.

The sources of noble elements of group VIII that can advantageously be used are well known to one skilled in the art. For the noble metals, halides are used, for example chlorides, nitrates, acids such as chloroplatinic acid, hydroxides, and oxychlorides such as ammoniacal ruthenium oxychloride. It is also advantageously possible to use the cationic complexes such as the ammonium salts when it is desired to deposit platinum on the IZM-2 solid by cation exchange.

The thus obtained catalysts are shaped in the form of grains of different shapes and sizes. They are used in general in the form of cylindrical or multilobed extrudates, such as bilobed, trilobed, multilobed extrudates of straight or twisted shape, but they can optionally be manufactured and employed in the form of crushed powders, tablets, rings, balls, and wheels. Techniques other than extrusion, such as pelletizing or tabletting, can advantageously be used.

Preferably, the catalysts that are employed in the process according to the invention have the shape of spheres or extrudates. It is advantageous, however, that the catalyst comes in the form of extrudates with a diameter of between 0.5 and 5 mm, and more particularly between 0.7 and 2.5 mm. The shapes are cylindrical (which can be hollow or not), braided cylindrical, or multilobed (2, 3, 4 or 5 lobes, for example), rings. The cylindrical shape is advantageously used in a preferred manner, but any other shape can advantageously be used.

In the event that the catalyst that is used in the process according to the invention comprises at least one noble metal, the noble metal that is contained in said catalyst should be reduced. The reduction of the metal is advantageously carried out by the treatment under hydrogen at a temperature of between 150° C. and 650° C. and a total pressure of between 0.1 and 25 MPa. For example, a reduction consists of a plateau level at 150° C. of two hours and then a rise in temperature of up to 450° C. at the rate of 1° C./minute, and then a plateau level of two hours at 450° C.; during this entire reduction stage, the hydrogen flow rate is 1,000 normal $m^3$ of hydrogen per $m^3$ of catalyst, and the total pressure is kept constant at 0.1 MPa. Any ex-situ reduction method can advantageously be considered.

In the event that the catalyst that is used in the process according to the invention comprises at least one metal of group VIB in combination with at least one non-noble metal of group VIII, the metals are preferably used in their sulfurized form. The sulfurization of the catalyst can be carried out in situ or ex situ by any method that is known to one skilled in the art.

Conversion Process

The paraffinic feedstock that has a number of carbon atoms of between 9 and 25 and is produced from renewable resources is brought into contact, in the presence of hydrogen, with said catalyst at operating temperatures and pressures that advantageously make it possible to carry out a conversion and preferably a hydroisomerization that make it possible to achieve the targeted cold properties.

In accordance with the invention, said process is carried out at a temperature of between 150 and 500° C., at a pressure of between 0.1 MPa and 15 MPa, at an hourly volumetric flow rate of between 0.1 and 10 $h^{-1}$, and in the presence of a total quantity of hydrogen mixed with the feedstock such that the hydrogen/feedstock ratio is between 70 and 2,000 $Nm^3/m^3$ of feedstock.

Preferably, said process is carried out at a temperature of between 150° C. and 450° C. and in a very preferred manner between 200 and 450° C.; at a pressure of between 0.2 and 15 MPa, preferably between 0.5 and 10 MPa, and in a very preferred manner between 1 and 9 MPa; at an hourly volumetric flow rate that is advantageously between 0.2 and 7 $h^{-1}$, and in a preferred manner between 0.5 and 5 $h^{-1}$; and in the presence of a total quantity of hydrogen mixed with the feedstock such that the hydrogen/feedstock ratio is between 100 and 1,500 normal $m^3$ of hydrogen per $m^3$ of feedstock and preferably between 150 and 1,500 normal $m^3$ of hydrogen per $m^3$ of feedstock.

Preferably, the effluent that is obtained from the conversion process according to the invention is subjected at least in part, and preferably completely, to one or more separations. The object of this stage is to separate the gases from the liquid and in particular to recover the hydrogen-rich gases that may also contain light compounds such as the $C_1$-$C_4$ fraction and at least one diesel fuel base and/or a kerosene base, and preferably a kerosene base.

Products Obtained.

The product that is provided according to this process is endowed with excellent characteristics, which thereby create a diesel fuel base of excellent quality:

Its sulfur content is less than 10 ppm by weight,
Its total content of aromatic compounds is less than 5% by weight, and the content of polyaromatic compounds is less than 2% by weight,
The cetane index is excellent, greater than 55,
The density is less than 840 $kg/m^3$, and most often less than 820 $kg/m^3$,
Its kinematic viscosity at 40° C. is 2 to 8 $mm^2/s$,
Its cold strength properties are compatible with the standards in force.

The kerosene base that is obtained according to the process is also of excellent quality:

Its sulfur content is less than 10 ppm by weight,
Its total content of aromatic compounds is less than 5% by weight, and the content of polyaromatic compounds is less than 2% by weight,
Its smoke point is greater than 21 mm,
Its cold properties are compatible with the standards in force,
The density is less than 840 $kg/m^3$, and most often less than 820 $kg/m^3$.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French Application No. 11/04024, filed Dec. 22, 2011 are incorporated by reference herein.

EXAMPLES

Example 1

Preparation of the Paraffinic Feedstock

The paraffinic feedstock is obtained by hydrotreatment of a canola oil of grade DNS (degummed, neutralized and dried). The catalyst that is used for carrying out the hydrotreatment is an NiMoP/alumina sulfurized catalyst that comprises 0.22% by weight of NiO, 21% by weight of $MoO_3$, and 5% by weight of $P_2O_5$ supported on a gamma-alumina. Said catalyst as well as the operating conditions employed for this hydrotreatment stage are described in the patent FR 2 943 071. The effluent that is obtained from the hydrotreatment is then sent into a separator that makes it possible to separate the water, the unconverted hydrogen, and the gases that are formed, and in particular propane, CO and $CO_2$, $H_2S$, and $NH_3$, and to produce a paraffinic feedstock that consists of 90% by weight of normal paraffins with 17 and 18 carbon atoms. An analysis by simulated distillation shows that this paraffinic feedstock does not contain molecules that boil at less than 150° C.

Example 2

Preparation of the Hydroisomerization Catalyst C1 (Non-Compliant)

The catalyst C1 is a catalyst that contains a noble metal and a three-dimensional 12 MR zeolite. It involves a USY commercial zeolite, the CBV760 zeolite, provided by the ZEOLYST Company. This zeolite has an Si/Al atomic ratio (determined by X fluorescence) of 30. This zeolite is mixed with an SB3-type alumina gel that is provided by the Condéa-Sasol Company. The mixed paste is extruded through a die of 1.4 mm. After drying in an oven for one night at 110° C., the extrudates are calcined at 500° C. for two hours (temperature rise slope of 5° C./min) in a bed flushed under dry air (2 normal liters per hour and per gram of solid). The extrudates are then impregnated in the dry state by an aqueous solution of tetraamine platinum nitrate $Pt(NH_3)_4(NO_3)_2$, allowed to mature in a water soaker for 24 hours at ambient temperature, and then calcined at 500° C. (temperature rise slope of 5° C./min) for two hours in a bed flushed under dry air (2 normal liters per hour and per gram of solid). The contents by weight of the CBV760 zeolite and platinum on the finished catalyst after calcination are respectively 15% and 0.32% by weight.

Example 3

Preparation of the Hydroisomerization Catalyst C2 (Non-Compliant)

The catalyst C2 is a catalyst that contains a noble metal and a mono-dimensional 10 MR zeolite, ZBM-30. This zeolite is synthesized in accordance with the patent BASF EP-A-46504 with the organic structuring agent triethylenetetramine. The crude synthesis zeolite is then subjected to calcination at 550° C. for 12 hours (temperature rise slope of 5° C./min) in a bed flushed under dry air (2 normal liters per hour and per gram of solid). The zeolite that is obtained has an Si/Al atomic ratio (determined by X fluorescence) of 45. The shaping of the zeolite with the alumina gel SB3 as well as the deposition of platinum are carried out under the same conditions as for the catalyst C1. The contents by weight of the zeolite ZBM30 and platinum on the finished catalyst after calcination are respectively 14% and 0.35% by weight.

Example 4

Preparation of the Hydroisomerization Catalyst C3 (Non-Compliant)

The catalyst C3 is a catalyst that contains a noble metal and a mono-dimensional 10 MR zeolite, ZSM-22. This zeolite is synthesized according to the method of Ernst et al. (Applied Catalysis, 1989, 48, 137). The crude synthesis zeolite is treated thermally at 400° C. for five hours (temperature rise slope of 5° C./min) in a bed flushed under nitrogen (0.6 normal liter per hour and per gram of solid) and then at 550° C. for 16 hours (temperature rise slope of 5° C./min) under oxygen (0.6 normal liter per hour and per gram of solid). The solid is then put under reflux for 4 hours in an ammonium chloride solution (100 ml of solution per gram of solid, concentration of ammonium chloride of 0.5 M) so as to exchange the alkaline cations by ammonium ions. Finally, the solid is washed with distilled water so as to eliminate the alkaline chloride (test with negative silver nitrate), and then dried for one night in an oven at 60° C. The zeolite that is obtained has an Si/Al atomic ratio (determined by X fluorescence) of 30. The shaping of the zeolite with the alumina gel SB3 as well as the deposition of platinum are carried out under the same conditions as for the catalyst C1. The contents by weight of the ZSM-22 zeolite and platinum on the finished catalyst after calcination are respectively 18% and 0.31% by weight.

Example 5

Preparation of the Hydroisomerization Catalyst C4 (Compliant)

The catalyst C4 is a catalyst that contains a noble metal and the IZM-2 zeolite. This IZM-2 zeolite has been synthesized in accordance with the teaching of the patent application FR 2 918 050. The crude synthesis IZM-2 zeolite then undergoes calcination at 550° C. for ten hours (temperature rise slope of 5° C./min) in a bed flushed under dry air (2 normal liters per hour and per gram of solid). The solid that is obtained is put under reflux for 4 hours in an ammonium nitrate solution (100 ml of solution per gram of solid, ammonium chloride concentration of 10 M) so as to exchange alkaline cations by ammonium ions. This refluxing stage is carried out four times. The thus obtained solid has an Si/Al ratio (determined by X fluorescence) of 53. The shaping of the zeolite with the alumina gel SB3 as well as the deposition of platinum are carried out under the same conditions as for the catalyst C1. The contents by weight of the IZM-2 zeolite and the platinum on the finished catalyst after calcination are respectively 20% and 0.32% by weight.

Example 6

Hydroisomerization of the Paraffinic Feedstock—Production of Diesel Fuel Base

The paraffinic feedstock that is obtained in Example 1 is hydroisomerized on the different hydroisomerization catalysts in a flushed bed in a hydroisomerization reactor that operates under isothermal conditions and on lost hydrogen. Before the catalytic test, each catalyst undergoes a reduction stage under a stream of hydrogen under the following operating conditions:

Total pressure: 0.1 MPa,
Hydrogen flow rate: 1,600 normal liters per hour and per liter of catalyst,
Rise in ambient temperature to 120° C. at 10° C./minute,
Plateau of one hour at 120° C.,
Rise from 120° C. to 450° C. at 5° C./min,
Plateau of two hours at 450° C.

The paraffinic feedstock is hydroisomerized on the different catalysts under the following operating conditions:

Total pressure: 5 MPa,
VVH (volume of feedstock/volume of catalyst/hour): 1 $h^{-1}$,
Hydrogen/feedstock ratio: 700 normal liters/liter,
Temperature: variable The reaction temperature is adjusted in such a way as to obtain a boundary temperature of filterability of the 150° C.$^+$ fraction of the hydroisomerized effluent of close to −40° C.

The yields of the 150° C.$^-$ fraction and the 150° C.$^+$ fraction (obtained by simulated distillation) of the effluent as well as the boundary temperature of filterability (obtained by the NF EN 116 method) of the 150° C.$^+$ fraction of the effluent are recorded for all of the catalysts in Table 1. It is noted that for all of the catalysts, it is possible to obtain a diesel fuel base that has excellent cold strength properties but the use of the catalyst C4 in accordance with the invention makes it possible to limit the formation of light products (150° C.$^-$ fraction).

TABLE 1

| Catalyst | C1 | C2 | C3 | C4 |
|---|---|---|---|---|
| % by Weight of the 150° C.$^-$ Fraction | 30 | 15 | 20 | 11 |
| % by Weight of the 150° C.$^+$ Fraction | 70 | 85 | 80 | 89 |
| Boundary Temperature of Filterability/° C. | −38 | −42 | −39 | −40 |

Example 7

Hydroisomerization of the Paraffinic Feedstock—Production of Kerosene Base

The paraffinic feedstock that is obtained in Example 1 is hydroisomerized on the different catalysts according to the protocol defined in Example 6, with the test temperature being adjusted here to obtain a disappearance point of the crystals of the 150° C.$^+$ fraction of close to −40° C.

The yields of the 150° C.$^-$ fraction and the 150° C.$^+$ fraction (obtained by simulated distillation) of the effluent as well as the disappearance point of the crystals (obtained by the ASTM D7153 method) of the 150° C.$^+$ fraction of the effluent are recorded for all of the catalysts in Table 2.

TABLE 2

| Catalyst | C1 | C2 | C3 | C4 |
|---|---|---|---|---|
| % by Weight of the 150° C.$^-$ Fraction | 40 | 23 | 30 | 20 |
| % by Weight of the 150° C.$^+$ Fraction | 60 | 77 | 70 | 80 |

TABLE 2-continued

| Catalyst | C1 | C2 | C3 | C4 |
|---|---|---|---|---|
| Disappearance Point of the Crystals/° C. | −40 | −42 | −41 | −41 |

It is noted that for all of the catalysts, it is possible to obtain a kerosene base that has excellent cold strength properties, but the use of the catalyst C4 in accordance with the invention makes it possible to limit the formation of light products (150° C.⁻ fraction).

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A hydroisomerization process for conversion of a paraffinic feedstock that has a number of carbon atoms of 10 to 22, wherein said paraffinic feedstock that has a number of carbon atoms of 10 to 22 is produced starting from renewable resources, excluding paraffinic feedstocks that are obtained by a process that involves a stage for upgrading by the Fischer-Tropsch method, wherein said hydroisomerization process is performed in the presence of a catalyst that comprises at least one hydrogenating-dehydrogenating noble metal of group VIII of the periodic table, a substrate comprising at least one IZM-2 zeolite and at least one binder, and 0.1 to 0.5% by weight of tin relative to the total catalyst mass, wherein said process is carried out at a temperature of between 150 and 500° C., at a pressure of between 0.1 MPa and 15 MPa, at an hourly volumetric flow rate of between 0.1 and 10 h$^1$, and in the presence of a total quantity of hydrogen that is mixed with the feedstock such that the hydrogen/feedstock ratio is between 70 and 2,000 Nm$^3$/m$^3$ of feedstock.

2. A process according to claim 1, in which said paraffinic feedstock is produced from a renewable resource that is a vegetable oil, alga or algal oil, fish oil, or fat of vegetable or animal origin, or a mixture thereof.

3. A process according to claim 1, in which the catalyst further comprises at least one hydrogenating-dehydrogenating metal element of group VIII, which is cobalt or nickel, or a mixture thereof, and wherein the noble metal of group VIII is platinum, palladium, or a mixture thereof.

4. A process according to claim 3, in which the catalyst has a content of noble metal of between 0.01 and 5% by weight relative to the total mass of said catalyst.

5. A process according to claim 1, in which the catalyst further comprises at least one hydrogenating-dehydrogenating metal element of group VIB, which is tungsten or molybdenum, or a mixture thereof.

6. A process according to claim 1, in which the catalyst further comprises at least one hydrogenating-dehydrogenating metal element of group VIB at a content of between 5 and 40% by weight of oxide relative to the total mass of said catalyst, and at least one hydrogenating-dehydrogenating metal element of non-noble metal of group VIII at a content of between 0.5 and 10% by weight of oxide relative to the total mass of said catalyst.

7. A process according to claim 1, in which said catalyst comprises 2 to 80% by weight of IZM-2 zeolite relative to the total mass of said catalyst.

8. A process according to claim 1, in which said binder is alumina, silica, silica-alumina, clay, titanium oxide, boron oxide, or zirconia, or a mixture thereof.

9. A process according to claim 8, in which said catalyst comprises 5 to 98% by weight of binder relative to the total mass of said catalyst.

10. A process according to claim 1, in which said process is carried out at a temperature of between 150° C. and 450° C., at a pressure of between 0.2 and 15 MPa, at an hourly volumetric flow rate of between 0.2 and 7 h$^{-1}$, and in the presence of a total quantity of hydrogen mixed with the feedstock such that the hydrogen/feedstock ratio is between 100 and 1,500 normal m$^3$ of hydrogen per m$^3$ of feedstock.

11. A process according to claim 1, in which said paraffinic feedstock has a number of carbon atoms of between 10 and 21.

12. A process according to claim 1, in which said paraffinic feedstock has a number of carbon atoms of between 10 and 20.

13. A process according to claim 1, in which said paraffinic feedstock has a number of carbon atoms of between 17 and 18.

14. A process according to claim 1, in which said catalyst comprises 0.1% by weight of tin relative to the total catalyst mass.

15. A process according to claim 1, in which said catalyst comprises 0.5% by weight of tin relative to the total catalyst mass.

* * * * *